United States Patent [19]

Gibson et al.

[11] 4,149,957
[45] Apr. 17, 1979

[54] SEPARATION APPARATUS

[75] Inventors: John A. Gibson, Abingdon; Michael J. Smyth, Newbury; Derek J. Steptoe, Abingdon, all of England

[73] Assignee: United Kingdom Atomic Energy Authority, London, England

[21] Appl. No.: 929,543

[22] Filed: Jul. 31, 1978

[30] Foreign Application Priority Data

Aug. 17, 1977 [GB] United Kingdom ............... 34600/77

[51] Int. Cl.² ............................................. B01D 13/02
[52] U.S. Cl. ................................ 204/301; 204/180 R; 204/180 P; 204/299 R; 204/300 R
[58] Field of Search ............... 204/180 R, 180 P, 299, 204/300, 301

[56] References Cited

U.S. PATENT DOCUMENTS

| 670,351 | 3/1901 | Schwerin | 204/301 |
| 1,034,668 | 8/1912 | Wright | 204/304 |
| 1,558,382 | 10/1925 | Marx | 204/180 R |
| 2,500,878 | 3/1950 | Sieling | 204/180 R |
| 2,739,938 | 3/1956 | Wiechers | 204/301 |
| 3,197,394 | 7/1965 | McEven | 204/180 R |
| 3,616,453 | 10/1971 | Philpot | 204/299 |
| 3,844,926 | 10/1974 | Smyth et al. | 204/300 X |

Primary Examiner—Arthur C. Prescott
Attorney, Agent, or Firm—Larson, Taylor and Hinds

[57] ABSTRACT

An electrophoretic separation apparatus of the type described in U.S. Pat. No. 3,844,926 wherein the means for generating the electric field is constituted by an anode system and a cathode system, said systems being positioned on opposite sides of the annular separation chamber to one another and one or both of said systems comprising a semi-permeable membrane which defines the annular separation chamber, at least in part, and which is supported by a water-permeable resin-bonded cellulose fibre material, means for contacting said material with an electrolyte, and an electrode for supplying an electric current to the electrolyte.

5 Claims, 2 Drawing Figures

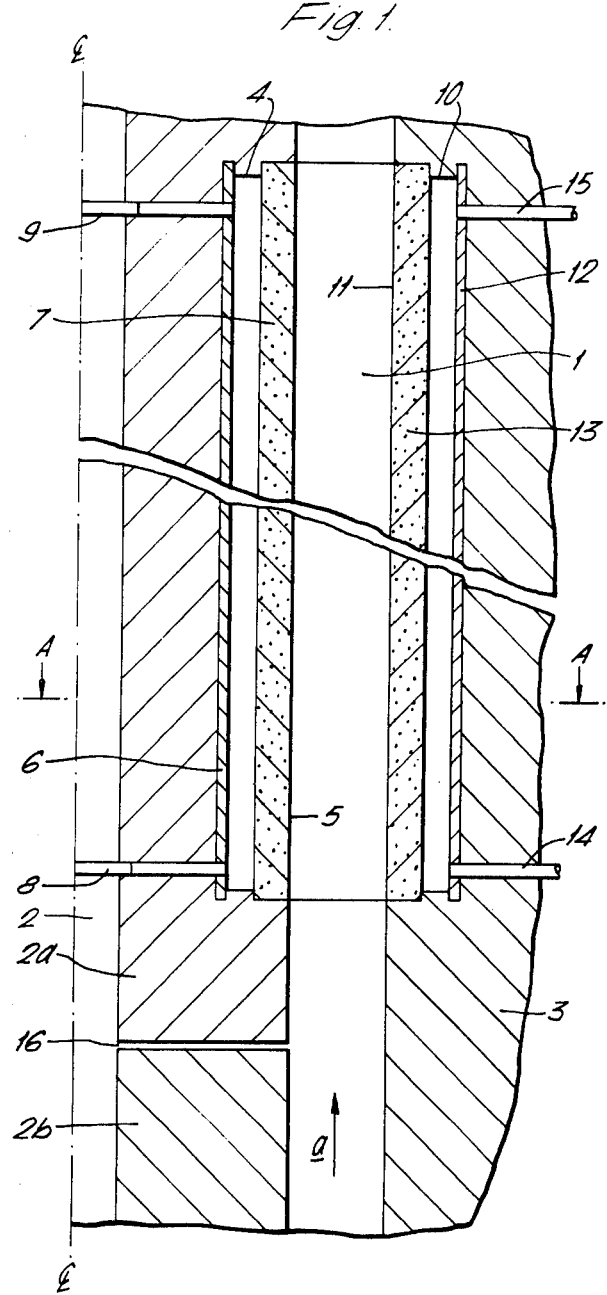

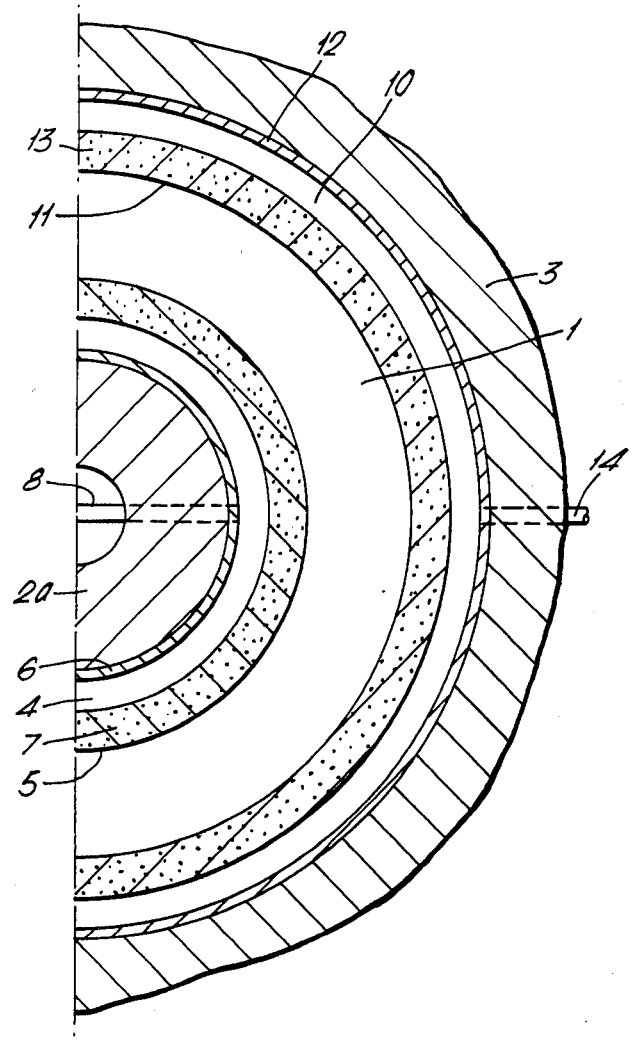

SEPARATION APPARATUS

This invention relates to an electrophoretic separation apparatus.

An electrophoretic separation apparatus is known which comprises an annular separation chamber defined by a central cylinder and an outer cylinder; an inlet for supplying migrant solution to the chamber and situated at or near the bottom of the chamber; an inlet for providing a carrier solution to transport the migrant solution upwardly through the separation chamber; means for generating an electric field across the chamber thereby to separate the migrant solution into fractions or differing electrophoretic mobilities; and means for collecting the separated fractions. Such an apparatus will be referred to herein as an electrophoretic separation apparatus of the kind described. Preferably the outer cylinder (termed the 'rotor' in this case) is rotatable about the inner cylinder (the 'stator') in order to stabilise the flow conditions in the chamber thereby increasing throughput whilst operating continuously.

Such apparatus is described, for example, in U.S. Pat. No. 3,844,926 and examples of its application are in the fractionation and/or purification of a wide range of biologically active materials, including macromolecules and sub-cellular particles.

In operation of an electrophoretic separation apparatus of the kind described, it is important to avoid perturbations in the carrier flow in the separation chamber in order to preserve its laminarity, otherwise, the resolution of the fractions is deleteriously affected. To meet this problem, access of gas bubbles to the chamber from the means for generating the electric field must be completely prevented. We have now devised a way of doing this in a particularly advantageous way.

Thus, according to the present invention, there is provided an electrophoretic separation apparatus of the kind described wherein the means for generating the electric field is constituted by an anode system and a cathode system, said systems being positioned on opposite sides of the annular separation chamber to one another and one or both of said systems comprising a semi-permeable membrane which defines the annular separation chamber, at least in part, and which is supported by a water-permeable resin-bonded cellulose fibre material, means for contacting said material with an electrolyte, and an electrode for supplying an electric current to the electrolyte.

We have found that, in operation of an apparatus according to our invention, there is little or no generation of perturbations in the chamber arising from the generation of the electric field. Thus the semi-permeable membrane effectively prevents access of gas bubbles to the chamber by separating the carrier from the electrolyte during operation.

The resin bonded cellulose fibre material used in the present invention has a number of advantageous features as follows: it has adequate strength when immersed in an electrolyte sufficient to maintain dimensional stability; it is capable of being easily and accurately machined to small tolerances; it is not significantly attacked by moderate concentrations of a variety of inorganic salts and is resistant to attack over a pH range of from 2 to 12; it is not bio-degradable, nor is it significantly attacked by biological solutions which might be used as migrant; it does not promote degradation of biological material; it has a low electrical resistance when immersed in an electrolyte; and it has a high void fraction. The latter two are inter dependent and can be expressed in terms of a resistance factor which is the increase in electrical resistance of electrolyte saturated material compared with that of a section of the electrolyte of similar dimensions.

The cathode system may be housed in the central cylinder of the apparatus and the anode system in the outer cylinder, or vice versa. The semi-permeable membrane of the particular system separates the electrolyte from the carrier during operation.

The invention will now be particularly described by way of example only with reference to the drawings accompanying the provisional specification where FIG. 1 is a sectional side elevation of a part of an electrophoretic separation apparatus incorporating our invention; and FIG. 2 is a section on the line A–A of FIG. 1.

The figures show one half of the apparatus about the centre line shown in FIG. 1.

Referring to FIGS. 1 and 2, an annular separation chamber 1 is defined between a rigidly mounted cylindrical stator 2 and cylindrical rotor 3 provided with a drive shaft (not shown) by means of which it may be rotatably driven. The stator 2 is in two parts, 2a and 2b, between which a migrant inlet 16 for supplying migrant solution to the separation chamber 1 is defined.

Recessed within the stator 2 is a cathode system comprising an electrolyte compartment 4 bounded on its outer side by a semi-permeable cellulose membrane 5, which is permeable to ions and which defines part of the separation chamber 1, and on its inner side by a stainless steel electrode 6. The membrane 5 is supported by a cylindrical porous support 7 fabricated from cellulose fibre bonded by a phenolic resin. The electrolyte compartment 4 has inlet and outlet tubes 8 and 9 for electrolyte.

Recessed within the rotor 3 is an anode system comprising an electrolyte compartment 10 bounded on its outer side by a semi-permeable cellulose membrane 11, which is permeable to ions and which defines part of the separation chamber 1, and on its outer side by a stainless steel electrode 12. The membrane 11 is supported by a cylindrical porous support 13 fabricated from cellulose fibre bonded by a phenolic resin. The electrolyte compartment 10 has inlet and outlet tubes 14 and 15 for electrolyte.

In operation, a carrier solution passes upwardly through the separation chamber 1 in the direction shown by the arrow a. Migrant is injected through the migrant inlet 16 and thus into the carrier stream. An electrolyte is supplied to the electrolyte compartment 4 through the inlet 8 and leaves through the outlet 9. Also, an electrolyte is supplied to the electrolyte compartment 10 through the inlet 14 and leaves through the outlet 15. At the same time, the electrode 6 is connected as cathode to a source of e.m.f. and the electrode 12 is connected as the anode to a source of e.m.f. Also, the rotor 3 is rotated about the stator 2 by means of the drive shaft (not shown).

The migrant is carried by the carrier stream in a helical flow pattern into the region of the separation chamber 1 bounded by the semi-permeable membranes 5 and 11, where it is electrophoretically separated into fractions of differing electrophoretic mobility, which are subsequently collected. The use of the porous supports 7 and 13 defines the separation chamber 1 with high concentric accuracy. This enables maximum stabilisation of laminar flow to be achieved in the chamber 1 during operation. The combination of porous support 7 and membrane 5 and porous support 13 and membrane 11 prevents access of gas bubbles to the chamber 1 and hence inhibits disturbance of laminar flow conditions therein.

The porous supports 7 and 13 used were made from a "CUNO" filter cartridge which is fabricated from cellulose fibre bonded by phenolic resin. The pore size of the material was nominally 5 microns and the void fraction about 85%. The resistance factor was 4.1 which compares very favourably with the resistance factor of other porous materials viz. sintered $ZrO_2$: 17.1; porous polyethylene: 14.0; sintered glass: 9.2 (pore size 150 to 250$\mu$) and 8.5 (pore size 15 to 40$\mu$); sintered $Si_3N_4$: 5.0. A low resistance factor is necessary in order to reduce the electrical resistance heat generated at the boundaries of the annular separation chamber where the electrical field is generated. The effect of such heat is very detrimental as it tends to cause convective mixing. The reduction in heat generated in the resin bonded cellulose fibre material used in our invention permits greatly enhanced performance to be obtained from the separator.

("CUNO" is the proprietary name for filter catridges manufactured by AMF International Ltd.).

We claim:

1. An electrophoretic separation apparatus of the kind described wherein the means for generating the electric field is constituted by anode system and a cathode system, said systems being positioned on opposite sides of the annular separation chamber to one another and one or both of said systems comprising a semipermeable membrane which defines the annular separation chamber, at least in part, and which is supported by a water-permeable resin-bonded cellulose fibre material, means for contacting said material with an electrolyte, and an electrode for supplying an electric current to the electrolyte.

2. An electrophoretic separation apparatus according to claim 1 wherein each of said systems comprises a semi-permeable membrane which defines the annular separation chamber, at least in part, and which is supported by a water-permeable resin-bonded cellulose fibre material, means for contacting said material with an electrolyte, and an electrode for supplying a electric current to the electrolyte.

3. An electrophoretic separation apparatus according to claim 2 wherein the material is a phenolic resin bonded cellulose fibre material.

4. An electrophoretic separation apparatus according to claim 3 wherein the material has a pore size of 5 microns and a void fraction of 85%.

5. An electrophoretic separation apparatus according to claim 3 wherein the cathode system is housed in the central cylinder of the apparatus and the anode system in the outer cylinder.

* * * * *